United States Patent [19]

Possis et al.

[11] Patent Number: 4,562,597
[45] Date of Patent: Jan. 7, 1986

[54] METHOD OF SUPPLYING BLOOD TO BLOOD RECEIVING VESSELS

[75] Inventors: Zinon C. Possis; Demetre M. Nicoloff, both of Edina, Minn.

[73] Assignee: Possis Medical, Inc., Minneapolis, Minn.

[21] Appl. No.: 489,798

[22] Filed: Apr. 29, 1983

Related U.S. Application Data

[62] Division of Ser. No. 448,955, Dec. 13, 1982.

[51] Int. Cl.[4] ............................ A61F 1/24; A61F 1/00
[52] U.S. Cl. .................................. 623/1; 128/334 R; 3/1
[58] Field of Search ......................... 3/1.3, 1.4, 1.7, 1; 128/325, 327, 334 R, 334 C

[56] References Cited

U.S. PATENT DOCUMENTS

| | | |
|---|---|---|
| 2,127,903 | 8/1938 | Bowen . |
| 3,029,819 | 4/1962 | Starks . |
| 3,096,560 | 7/1963 | Liebig . |
| 3,166,688 | 1/1965 | Rowand et al. . |
| 3,490,975 | 1/1970 | Lightwood et al. . |
| 3,570,013 | 3/1971 | Blumen . |
| 3,626,947 | 12/1971 | Sparks . |
| 3,667,069 | 6/1972 | Blackshear et al. . |
| 3,730,186 | 5/1973 | Edmunds, Jr. et al. . |
| 3,805,301 | 4/1974 | Liebig . |
| 3,894,530 | 7/1975 | Dardik et al. . |
| 3,945,052 | 3/1976 | Liebig . |
| 3,974,526 | 8/1976 | Dardik et al. . |
| 3,988,782 | 11/1976 | Dardik et al. . |
| 4,240,794 | 12/1980 | Holman et al. . |
| 4,321,711 | 3/1982 | Mano . |
| 4,356,571 | 11/1982 | Esper et al. . |

OTHER PUBLICATIONS

Vargos et al.; "The Use of Nylon Net . . . "; Surgery, vol. 34, #6, 12/1953, pp. 1061–1075.
Hershey et al.; "Atlas of Vas. Sur."; p. 441; 1973.
"The Experimental Use of Heterologous Umbilical Vein Grafts as Aortic Substitutes", Singapore Medical Journal, vol. 3, No. 1, Mar. 1962.

Primary Examiner—Richard J. Apley
Assistant Examiner—Gregory Beaucage
Attorney, Agent, or Firm—Burd, Bartz & Gutenkauf

[57] ABSTRACT

A vascular graft is used to supply blood to one or more coronary artery branches. The vascular graft has an elongated U-shaped tubular body providing a continuous passage for carrying blood from a high pressure blood supply to a blood receiver. One or more openings in the body allow blood to flow into the coronary artery branches. The flow and pressure of the blood in the passage is controlled by a restriction providing a Venturi passage located remote from the inlet end of the tubular body. The restriction is reinforced with an annular sleeve to maintain a desired cross sectional area and length of the Venturi passage. The pressure differential between the blood supply and blood receiver maintains continuous and adequate blood flow at a desired pressure in the body passage and provides a continual supply of blood for the coronary artery branches.

10 Claims, 22 Drawing Figures

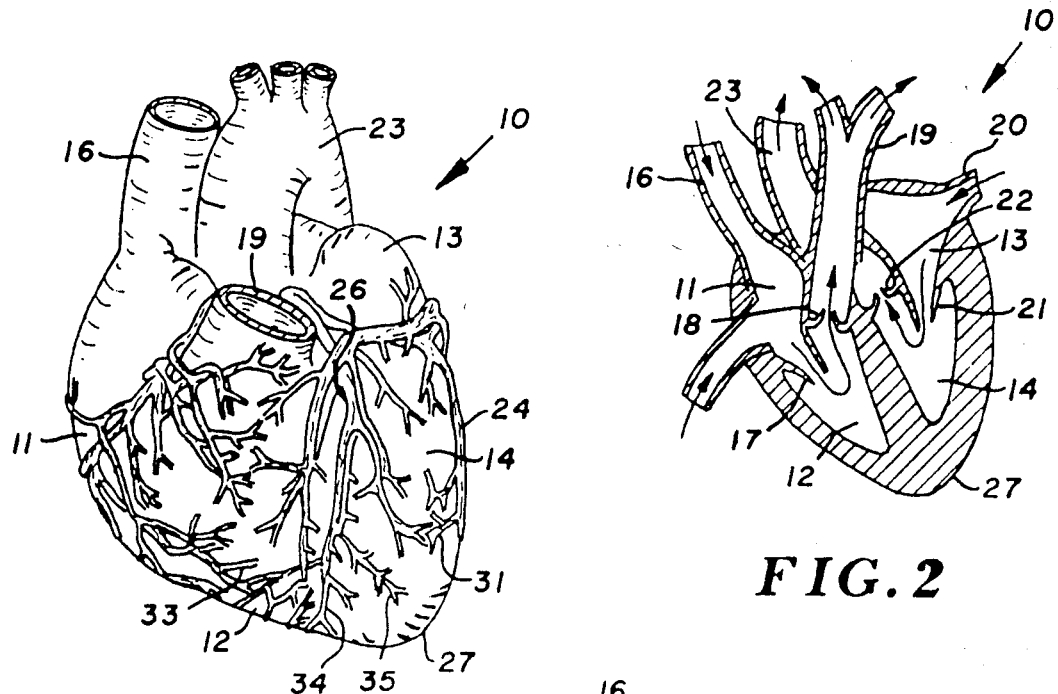
FIG. 1
FIG. 2
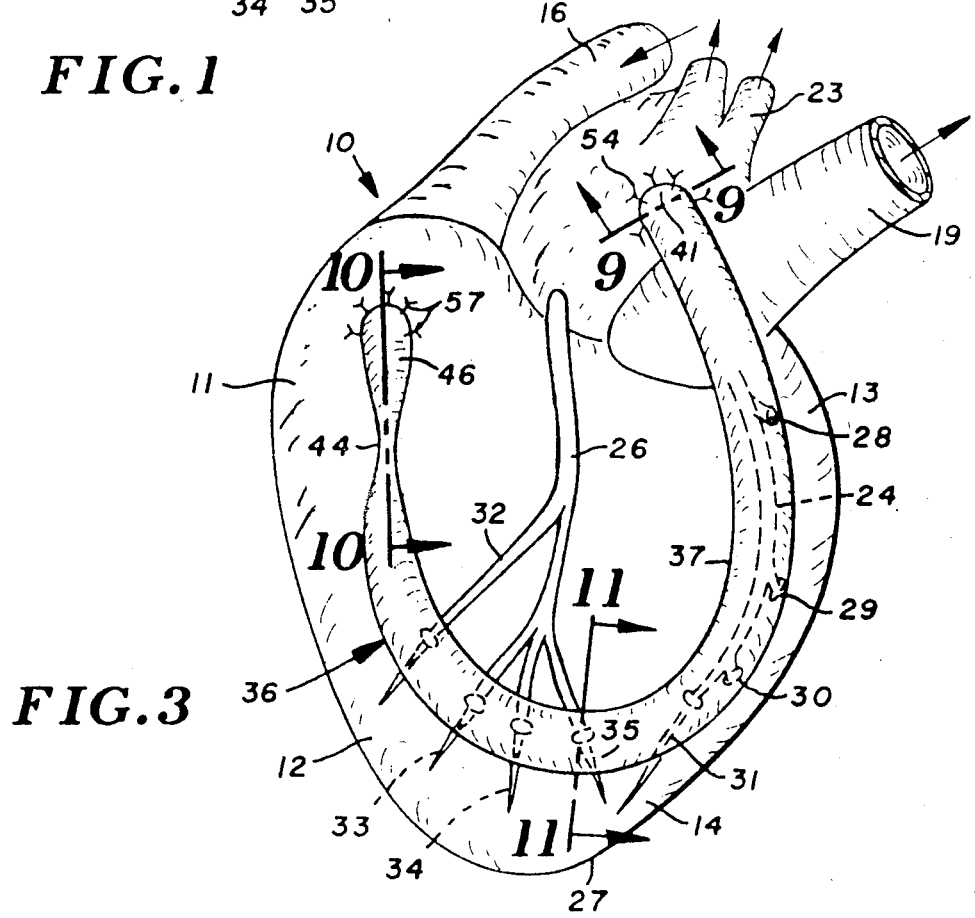
FIG. 3

METHOD OF SUPPLYING BLOOD TO BLOOD RECEIVING VESSELS

CROSS REFERENCE TO RELATED APPLICATION:

This application is a division of U.S. Application Ser. No. 448,955, filed Dec. 13, 1982.

FIELD OF INVENTION

The invention relates to implants used in the body to replace natural arteries to supply arterial blood to organs and tissues throughout the body. More particularly, the implants are vascular grafts used to supply blood to the tissue of the heart.

BACKGROUND OF THE INVENTION

The autogenous saphenous vein is used successfully as a vascular conduit for coronary artery revascularization. Although the search for a suitable prosthetic graft for aortocoronary bypass continuous, nothing better than the autogenous saphenous vein is available. Surgeons have been reluctant to use synthetic grafts in aortocoronary bypass because of few instances of long-term patency.

Although saphenous veins are used in aortocoronary bypass procedures, there are certain disadvantages: (1) unavailability, (2) small size, (3) non-uniform caliber, (4) varicosities, (5) large diameter, (6) sclerosis, (7) obstruction due to intimal hyperplasia, (8) aneurysm formation, (9) considerable time required for harvesting, (10) leg discomfort and swelling, and (11) possible leg infection.

A significant number of patients requiring aortocoronary bypass do not have suitable veins, or the veins have been used for previous aortocoronary bypass or for peripheral vascular bypass procedures. On occasion, the need for a graft may have been unforeseen prior to surgery, and the legs not prepared for harvesting of the vein. The cephalic vein from the arm has been used when the saphenous vein is not available. However, it is usually thin-walled and often of poor caliber. Furthermore, the cosmetic effect of harvesting the cephalic vein is unacceptable for some patients.

The internal mammary artery is widely accepted as suitable for myocardial revascularization, in that it has an excellent patency ratio, but is useful only for the left anterior descending and diagonal coronary arteries. Experience with free grafts of the internal mammary and radial arteries has been disappointing, since long-term patency has been poor.

The importance of the velocity of blood flow in autogenous vein grafts has been emphasized. There is evidence of an inverse relationship between the velocity of blood flow in venous grafts and the amount of intimal proliferation observed. Autopsy studies indicate that occlusion of aortocoronary saphenous vein grafts more than one month after operation is most commonly caused by fibrous intimal proliferation. Although the cause of this lesion has not been definitely established, studies would suggest that it is probably related to a low velocity of flow through the graft. This suggests that every effort should be made to achieve a high velocity of flow in coronary artery bypass grafts.

Synthetic vascular implants are disclosed by Liebig in U.S. Pat. Nos. 3,096,560; 3,805,301; and 3,945,052. These grafts are elongated knit fabric tubes made of yarn, such as polyester fiber. Dardik in U.S. Pat. No. 3,894,530 discloses the use of an umbilical cord for a vascular graft. Holman et al in U.S. Pat. No. 4,240,794 disclose a method of preparing human and other animal umbilical cords for use as a vascular replacement. The fabric tubes and umbilical cords have been used to replace the saphenous vein implant. The outlet ends of the tubes and cords are anastomosed to ends of arteries distal to diseased areas of the arteries. They replace the diseased portions of the arteries.

SUMMARY OF THE INVENTION

The goal of vascular reconstructive surgery is to effectively supply blood to organs and tissues whose blood vessels are obstructed by congenital defects or acquired disorders, such as arteriosclerosis, trauma, and other diseases. The invention is a vascular graft and a method employing the vascular graft for supplying arterial blood to organs and tissues throughout the body.

According to the invention, there is provided a graft for supplying blood to one or more blood receivers, such as blood vessels. The graft includes an elongated means having a continuous passage for carrying blood from a supply of blood under pressure to one or more blood receivers. The elongated means has a body providing a first passage for carrying of blood. The body has one or more openings and is connectable to at least one blood vessel for supplying blood to this blood vessel. The body has an inlet and means adapted to be connected to a supply of blood under pressure, whereby blood flows into the first passage and from the first passage into the blood vessel. The flow of blood and pressure of the blood in the first passage is controlled with a means having a restricted second passage connected to the distal portion of the body remote from the inlet end means. An outlet end means connects the means having the restricted second passage to blood receiving means. A pressure differential between the blood supply means and the blood receiving means maintains continuous and adequate blood flow at a desired pressure through the first and second passages and provides a continual supply of blood for the blood vessels that are attached to the body.

The graft is used to supply blood to one or more coronary artery branches in a human heart. The heart has two atria for receiving blood from the vena cava and pulmonary veins and is connected to an aorta to carry blood under pressure from the heart. The graft comprises an elongated generally U-shaped tubular means having a continuous longitudinal passage for carrying blood from the aorta to the right atrium. A tubular means has an inlet end anastomosed to the aorta so that blood under pressure flows from the aorta into the passage and is discharged through an outlet end into the right atrium. The outlet end of the tubular means is anastomosed to the heart tissue around an opening in communication with the right atrium. The tubular means has one or more openings used to provide blood to one or more coronary artery branches. The coronary artery branches are sutured to the tubular means whereby blood flows through the openings in the tubular means into the coronary artery branches. The flow and pressure of the blood in the passage is controlled by a restriction located remote from the inlet end of the tubular means. The restriction has a second throat passage having a diameter that is less than one-half the diameter of the main or first passage of the tubular means. The tubular means is generally U-shaped and encircles the critical areas of the heart beginning at the aorta and ending at either the right or left atrium or pulmonary artery. The pressure differential between the aorta and the atrium, approximately 90 mm Hg, causes a continuous flow of blood in quantities and at velocities that inhibit clotting, and provides a continuous supply of blood at a desired pressure to the artery branches connected to the tubular means.

In one form of the invention, the tubular means is an elongated generally U-shaped synthetic tube, such as a polytetrafluoroethylene tube or a Dacron tube. The tube is continuous and has a reduced section proximal to the distal or outlet end thereof. The reduced section provides the restricted passage for controlling the blood flow and sustaining the pressure of the blood in the first passage of the tubular means.

A second embodiment of the invention utilizes a human umbilical cord as the elongated means. The umbilical cord is formed to a generally U-shape to encircle the critical areas of the heart. The outlet or distal end of the cord has a reduced section to provide a restriction or throat passage for controlling the flow of blood through the cord. Selected arteries are anastomosed to the body of the cord and are provided with openings whereby blood from the lumen of the cord can flow into the arteries.

In a third embodiment of the invention, the elongated tubular means comprises an autogenous saphenous vein having a large enough caliber to assure adequate blood flow. The vein encircles the heart from the aorta and extends to the atrium. The distal or outlet end section of the vein accommodates an adjustable blood flow restrictor operable to reduce the cross sectional area of the vein passage to form a throat passage. The throat passage restricts the flow of blood in the vein passage while maintaining a continuous flow of blood at a desired pressure. Selected portions of the vein are anastomosed to coronary branch arteries to provide continuous flow of blood to these arteries.

The invention includes a method of providing a continuous supply of flowing blood at a desired pressure to one or more blood receiving vessels, such as coronary branch arteries of a primate. A graft having a blood flow restricting throat passage in the distal end section thereof is anastomosed to the aorta. The graft is placed adjacent the heart to locate portions thereof in proximity to selected coronary branch arteries. Selected portions of the graft are anastomosed to coronary branch arteries. The distal end of the graft is anastomosed to the atrium or low blood pressure section of the blood circulatory system. Blood under pressure continuously flows from the aorta into the graft, since there is a substantial blood pressure difference between the aorta and atrium. The throat passage prevents the flow of blood from being excessive and maintains the blood pressure in the graft passage at substantially the same as the aorta blood pressure. The coronary arteries are perfused with sufficient quantities of blood.

IN THE DRAWINGS

FIG. 1 is an anterior view of a human heart;

FIG. 2 is a schematic longitudinal sectional diagram of the heart of FIG. 1;

FIG. 3 is an anterior view of a human heart having the graft of the invention;

DESCRIPTION OF PREFERRED EMBODIMENTS

Figure 4:
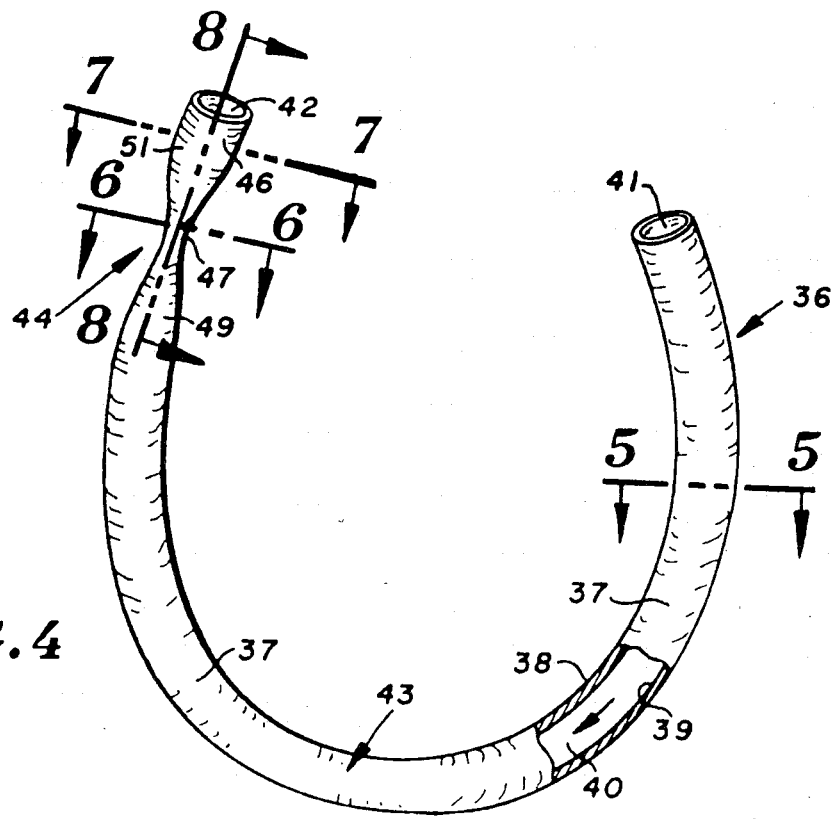
FIG. 4 is an enlarged partly sectioned plan view of the graft of FIG. 3.

Referring to FIGS. 1, 2 and 3, there is shown an anterior view of a human heart indicated generally at 10. Heart 10 has a right atrium 11, right ventricle 12, left atrium 13, and left ventricle 14. Blood from the body flows through vena ceva 16 into right atrium 11. The pressure of the blood in right atrium 11 is low as the blood flows into atrium 11. A heart valve 17 controls the flow of blood from atrium 11 into right ventricle 12. The blood is pumped from right ventricle 12 through valve 18 into pulmonary artery 19, which is connected to the lungs. The blood returns from the lungs via the pulmonary vein 20 to left atrium 13. The blood flows from left atrium 13 through heart valve 21 into a left ventricle 14 and is pumped from the left ventricle 14 through valve 22 into aorta 23. The pressure differential of the blood between aorta 23 and the atrium 11 is approximately 90 mm Hg. The muscle tissue of the heart is provided with a supply of blood from two coronary arteries 24 and 26. Left coronary artery 24 extends from aorta 23 along the left side of the heart toward the apex 17. Coronary artery 24 has a number of branches 28, 29, 30 and 31, which supply blood to the muscle tissue. Left coronary artery 24 has a short common stem which bifurcates or trifurcates into branches 28-21. One branch 31, the anterior interventricular branch, moves downward to the anterior interventricular groove and rounds the acute margin of the heart just to the right of apex 27 and ascends a short distance up the posterior interventricular groove. Portions of the branch 31 anastomose with branches from the right coronary artery. These branches are very small in normal hearts. They may enlarge considerably in persons suffering from coronary arteriosclerosis in whom coronary arterial branches become obstructed or occluded. The right coronary artery 26 extends down the right side of the heart toward the apex of crux 27. Artery 26 has a number of branches 32, 33, 34 and 35, which feed blood to the heart tissue.

The right coronary artery 26 arises from the right anterior sinus of aorta 23 and runs along the right atrioventricular sulcus. It rounds the acute margin to reach the crux. It has a number of branches 32–35 to the anterior right ventricle wall. The right arterial branches of the right coronary artery 26 originate from the right coronary artery shortly after its take-off and ascends along the anteromedial wall of the right atrium. Variations of the branching pattern of the arteries 24 and 26 are common in the human heart. In about 67% of the cases, the right coronary artery 26 is dominant and supplies part of the left ventricle wall and ventricle septum. In 15% of the cases, the left coronary artery 24 is dominant and supplies all of the left ventricle and the ventricle septum, and part of the right ventricle wall, with blood. In about 18% of the cases, both coronary arteries 24 and 26 reach the crux 27. It is common for the first, second and third branches of the right coronary artery 26 to originate independently from the right sinus, rather than the parent artery.

Figure 5:
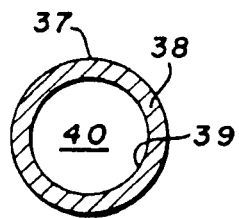
FIG. 5 is an enlarged sectional view taken along the line 5—5 of FIG. 4.
Figure 6:
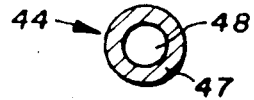
FIG. 6 is an enlarged sectional view taken along the line 6—6 of FIG. 4.
Figure 7:
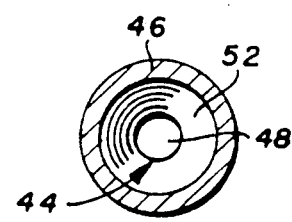
FIG. 7 is an enlarged sectional view taken along the line 7—7 of FIG. 4.

Referring to FIGS. 4–8, there is shown a vascular graft of the invention indicated generally at 36. Graft 36 is an elongated member 37 having a generally U-shape and a continuous passage 40 for carrying blood. Member 37 has a continuous cylindrical wall 38 having an inside surface 39 forming an elongated longitudinal passage 40. Tubular member 37 has a proximal aortic or inlet end 41 and a distal atrial or outlet end 42. A main generally U-shaped trunk 43 extends from inlet end 41 to a restricted or reduced section 44. Restricted section 44 is connected to a distal end section 46. Preferably, restricted section 44 is about 2 to 5 cm from outlet end 42 when it is attached to the heart tissue. As shown in FIGS. 5–7, restricted section 44 has a cylindrical wall 47 integral with cylindrical wall 38 of the main trunk 43 and atrial end section 46. Wall 47 surrounds a throat passage 48 having a cross sectional area substantially smaller than the cross sectional area of passage 40. The cross sectional area of passage 40 is preferably more than four times larger than the cross sectional area of throat passage 48. Cylindrical wall 47 is joined to wall 38 with a converging conical wall portion 49 which directs the flow of blood into passage 48. The opposite ends of wall 47 are joined to a diverging conical wall portion 51 forming parts of the atrial end section 46. Wall portion 51 surrounds an outlet passage 52 leading to the distal outlet end 42. The cross sectional area of outlet passage 52 is substantially the same as the cross sectional area of passage 40 of main trunk 43. Conical wall portions 49 and 51 each have a longitudinal length and an inside wall surface that has a gradual smooth taper to minimize turbulence in the blood flow. Preferably, cylindrical wall 47 surrounding passage 48 has a longitudinal length that is shorter than the longitudinal length of the wall portions 49 and 51. Other length and size relationships can be used. The longer the length of restricted section 44, the greater the blood pressure drop for a given cross sectional area of passage 48. Passage 52 provides a chamber wherein the velocity of the blood flow is decreased before it flows into the right atrium 11 of the heart. Distal end section 46 is of a size to permit easy attachment thereof to the heart tissue or blood receiving vessel.

The entire vascular graft 36 is a tubular structure, preferably made from a human umbilical cord. The umbilical cord can be pre-curved and tapered to form the desired restricted section 44 by processing. In use, it will not kink and is intimally lined. Other tubular structures, such as a polytetrafluoroethylene tube, can be used for vascular graft 36.

Figure 8:
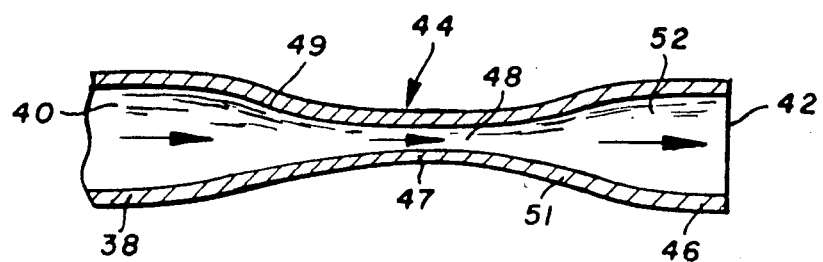
FIG. 8 is an enlarged sectional view taken along the line 8—8 of FIG. 4.
Figure 9:
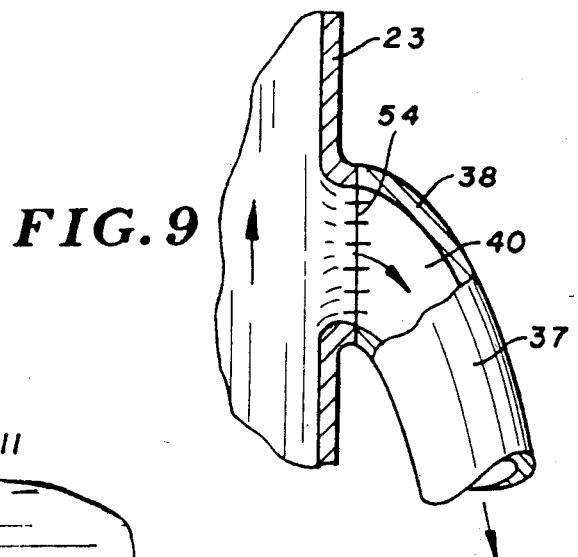
FIG. 9 is an enlarged sectional view taken along the line 9—9 of FIG. 3.
Figure 10:
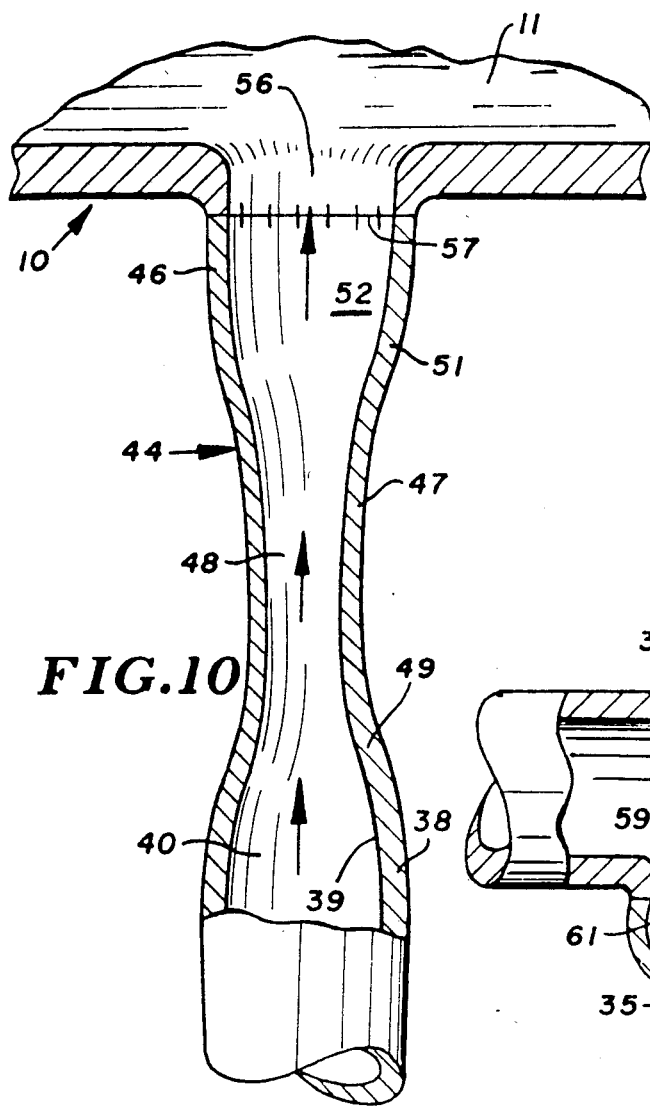
FIG. 10 is an enlarged sectional view taken along the line 10—10 of FIG. 3.

Referring to FIG. 3, vascular graft 36 is located adjacent the heart 10. Body 43 descends toward the midportion on the anterior surface of the heart and then encircles about to the posterior surface and ascends toward the right atrium. Restricted section 44 and atrial end section 46 are located adjacent atrium 11. As shown in FIG. 8, proximal or aortal end 41 of tubular member 37 is implanted into an aortic astium 53 and anastomosed thereto with sutures 54. As shown in FIG. 10, the outlet or atrial end 46 is attached to heart 10 around ostium 56 open to atrium 11 and anastomosed thereto with sutures 57. The blood continuously flows through passage 40 of tubular member 57, since the blood pressure difference between aorta 23 and atrium 11 is about 90 mm Hg. Restrictive throat passage 48 prevents the flow of blood through passage 40 from being excessive. The distal end section 16 of tubular member 37 can be anastomosed to the left atrium 13, whereby the blood flows from aorta 23 through the passages 40, 48 and 52 and into left atrium 13.

Figure 11:
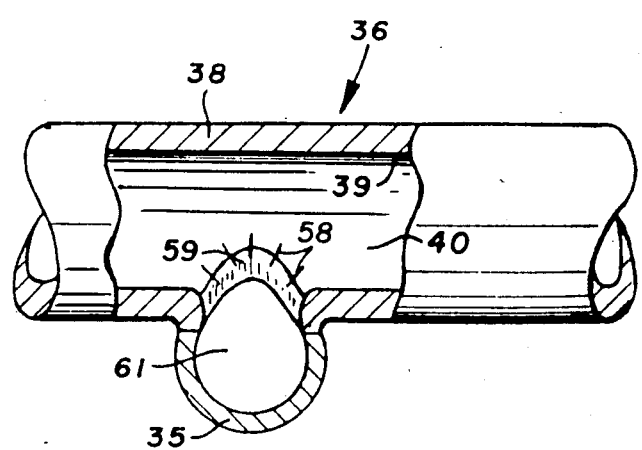
FIG. 11 is an enlarged sectional view taken along the line 11—11 of FIG. 3.
Figure 12:
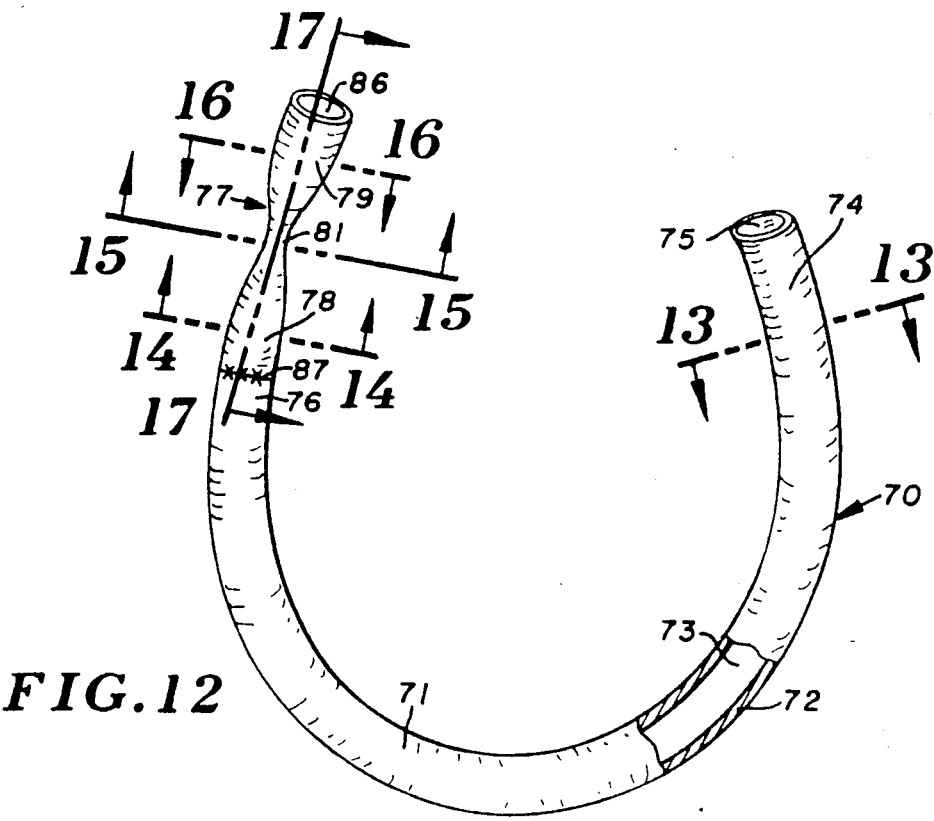
FIG. 12 is a plan view, partly sectioned of a saphenous vein and distal and tubular blood flow restrictor anastomosed to the vein, usable as a graft of the invention.
Figure 13:
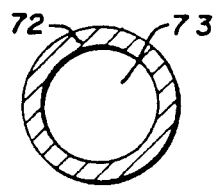
FIG. 13 is an enlarged sectional view taken along the line 13—13 of FIG. 12.
Figure 14:
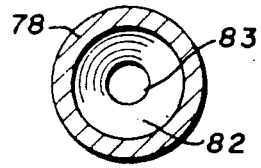
FIG. 14 is an enlarged sectional view taken along the line 14—14 of FIG. 12.
Figures 15, 16:
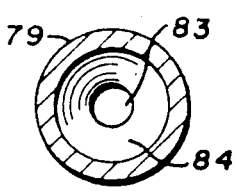
FIG. 15 is an enlarged sectional view taken along the line 15—15 of FIG. 12.
FIG. 16 is an enlarged sectional view taken along the line 16—16 of FIG. 12.
Figure 17:
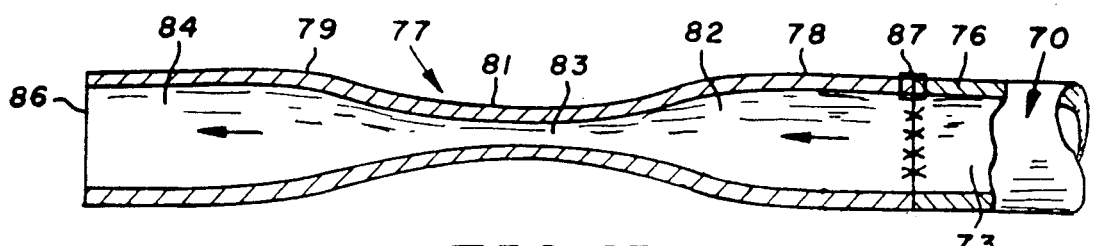
FIG. 17 is an enlarged sectional view taken along the line 17—17 of FIG. 12.
Figure 18:
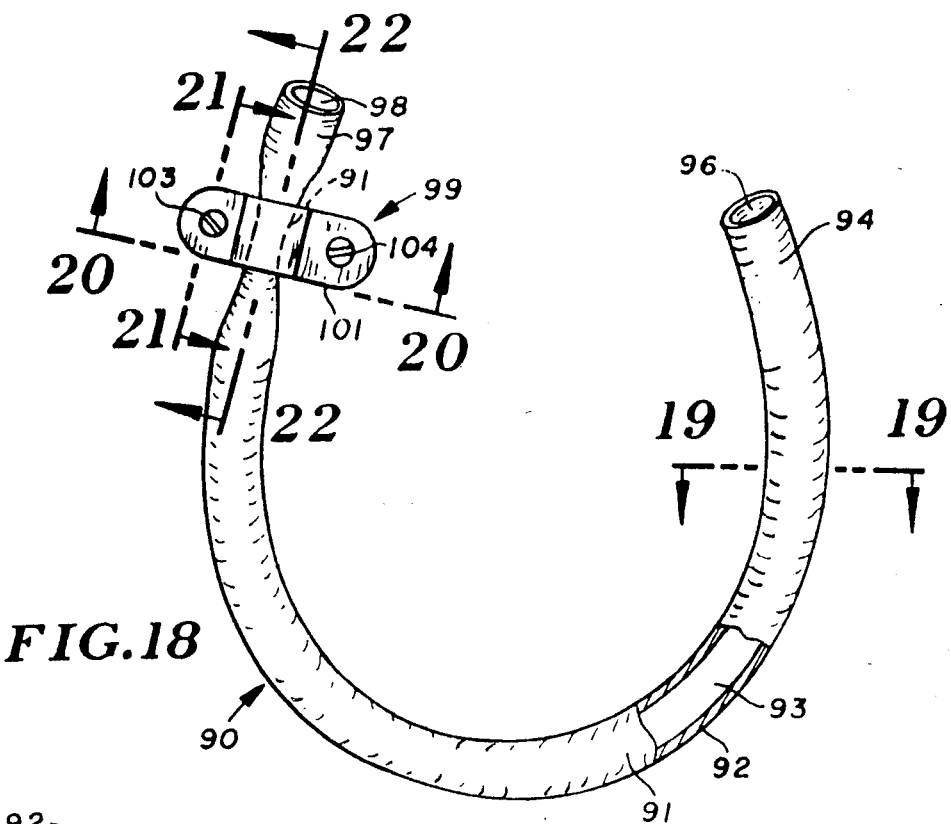
FIG. 18 is a plan view, partly sectioned, of a graft and adjustable blood flow restrictor therefor.
Figure 19:
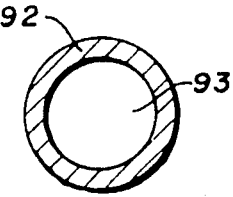
FIG. 19 is an enlarged sectional view taken along the line 19—19 of FIG. 1.
Figure 20:
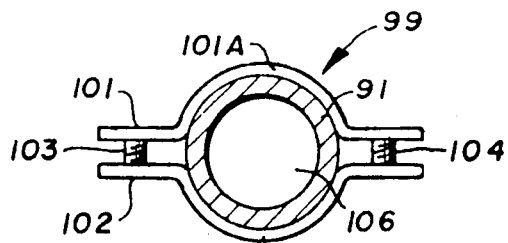
FIG. 20 is an enlarged sectional view taken along the line 20—20 of FIG. 18.
Figure 21:
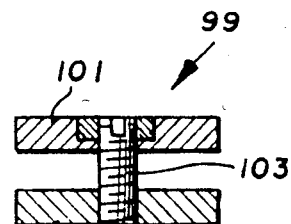
FIG. 21 is an enlarged sectional view taken along the line 21—21 of FIG. 18.

The body 43 of graft 36 is located adjacent one or more of the coronary branches 28–31 and 32–35. The surgeon has the option to anastomose and, therefore, perfuse one or more of the coronary branches along the path of the graft 36. Referring to FIG. 11, graft 36 is anastomosed to coronary branch 35 with sutures 58. The cylindrical wall 38 is provided with an opening 59 to allow blood to flow from passage 40 into the coronary artery passage 61. The restricted passage 48 adjacent the atrial end of the graft allows the coronary arteries to be perfused with sufficient quantities of blood at pressures within a few mm Hg of the aortic blood pressure. The flow of blood through restriction 48 is approximately laminar and continues as an approximate laminar flow through the passage 52 into atrium 11. There is a minimum of turbulence of the blood in graft 36. The interior surface 39 of the tubular member 37 is smooth and continuous. It does not have any pockets which can stagnate and coagulate the blood.

An adequate flow of blood through the graft passage 40 is insured by the diameter of the aortic anastomosis 53 of approximately 2500 ml per minute.

Tests indicate that, using a 5 mm diameter tubular graft with an aortic flow of approximately 6000 ml per minute and pressure of 1000 mm Hg, approximately 500 ml per minute will flow through a 2 mm restriction into the right atrium. Since the cardiac output is limited only by the venous return, the left ventricle will have an additional load of about 8 percent. Each coronary artery supplied with blood will require about 50 to 150 ml per minute of blood for adequate perfusion. Since the blood flow through an unrestricted 5 mm graft anastomosed to an aorta with blood flowing at 6000 ml per minute will provide blood flow well in excess of 2000 ml per minute, an adequate blood supply is available for up to 10 coronary branches, each carrying 150 mm per minute. Calculations of blood flow through the throat passage 48 show a Reynold's range of between 500 and 1000. The blood flow is approximately laminar in passages 50 and 48.

In certain cases, a surgeon may choose to use the autogenous saphenous vein in lieu of synthetic graft 36 over the umbilical cord, as described herein. Referring to FIGS. 12-17, there is shown a segment of an autogenous saphenous vein indicated generally at 70 comprising an elongated member 71. Member 71 has a continuous cylindrical wall 72 surrounding a passage or lumen 73 for accommodating flowing blood. The inlet or proximal end 74 of member 71 has anopening 75. The saphenous vein 70 has a generally U-shape and follows a path about the heart to reach occluded arteries in the manner of graft 36, as shown, in FIG. 3. Lumen 75 has a generally uniform diameter from the inlet or aorta end 74 to the distal end 76.

A blood flow restrictor or tubular segment indicated generally at 77 is anastomosed to distal end 76 of vein 70. Blood flow restrictor 77 has an inlet end section 78 and an outlet end section 79 joined to an intermediate throat section 81. Section 78 has an inlet plassage 82 longitudinally aligned with lumen 73. Inlet passage 82 communicates with a Venturi passage 83 in throat section 81. Venturi passage 83 opens to an outlet passage 84 in outlet end section 79. The cross sectional area of outlet passage 84 is substantially the same as the cross sectional area of the inlet passage 82. The sie of Venturi throat 83 can vary relative to the size of inlet passage 82. Preferably, the diameter of inlet passage 82 is more than twice the diameter of Venturi passage 83. The cross sectional area of passage 82 is more than four times the cross sectional area of throat passage 83. Venturi passage 83 allows the blood to continuously flow through lumen 73 at a desired blood pressure in lumen 77 so that one or more coronary artery branches can be perfused. The distal or atrial end section 79 has an open outlet 86 allowing blood to flow into the atrium of the heart when section 79 has been anastomosed to the atrium section of the heart.

In use, the surgeon harvests a section of the saphenous vein from the leg of the patient. A blood flow restrictor 77 having the desired size Venturi passage 83 is secured with sutures 87 to distal end 76 of tubular member 71. The aortal end 74 is anastoimosed to aorta 23. Tubular member 71 encircles the heart to locate atrium end 79 of restrictor 77 adjacent atrium 11. End 79 is anastomosed to the atrium section of the heart so that a continuous and adequate flow of blood is maintained through tubular member 70 and restrictor 77. The blood is at a desired pressure so that one or more coronary artery branches can be perfused. The surgeon can anastomose one or more coronary branches along the path of tubular member 70 in a manner, as shown in FIG. 11. This allows the continuous flow of blood under pressure from passage 73 into the lumen of the coronary branches.

Refering to FIGS. 18-22, there is shown a tubular graft indicated generally at 90 usable to continuously supply blood to one or more coronary artery branches of a human heart. Graft 90 has an elongated generally U-shaped member 91 having a continuous cylindrical wall 92. Wall 92 forms a generally uniform diameter passage 93. Member 91 has an aortic or proximal end 94 having an inlet opening 96 for receiving a continuous supply of blood from the aorta. The blood flows through passage 92 to a distal end 97 having an outlet opening 98. Distal end 97 is adapted to be anastomosed to the atrium section of the heart or a vein to receive blood therefrom.

Figure 22:
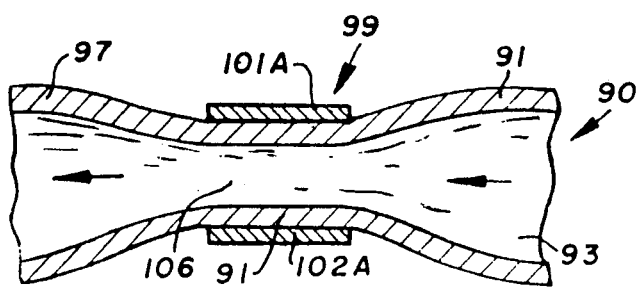
FIG. 22 is an enlarged sectional view taken along the line 22—22 of FIG. 18.

As shown in FIGS. 18-22, an adjustable blood flow restrictor indicated generally at 99 is mounted on member 91 adjacent distal end 97 for restricting the flow of blood into distal end 97 while maintaining a continuous and adequate flow of blood at a desired pressure so that one or more coronary artery branches can be perfused. Blood flow restrictor 99 is a clamp unit having a first member 101 adjustably connected to a second member 102 with a pair of self-locking screws 103 and 104. Member 101 has an outwardly curved center section 101A located about an arcuate sector of member 91. Second member 102 has an oppositely outwardly curved center section 102A facing the curved center section 101A and engageable with an arcuate segment of member 91. The screws 103 and 104 are adjustable to move the first and second members 101 and 102 toward each other to adjust the size of the Venturi throat passage 106, thereby adjusting the rate of flow of blood through passage 93 and adjusting the pressure of the blood in passage 93. A cylindrical mandrel having a desired cross sectional area is used to provide the throat passage with a desired size or cross sectional area. The mandrel is inserted into the distal end section of member 91. Restrictor 99 is placed over the distal end section and clamped onto member 91. The curved center sections 101A and 102A move toward each other and force the wall of the member about the mandrel. The mandrel is then removed from the member 91. Restrictor 99 maintains the selected cross section of throat passage 106, as shown in FIG. 22.

The grafts of the invention can be used to carry blood in peripheral revascularization procedures of the lower extremities. The graft would be interposed between the most distal arterial anastomosis and the popliteal vein or one of its major branches. The source of blood would be the femoral artery and the anastomosis would be made in the popliteal artery and/or its distal branches, the anterior tibia, posterior tibia, or peroneal arteries. The blood flow restricting passage or throat passage located between these arteries and the distal end of the graft controls the blood flow through the graft. The control of blood flow allows adequate perfusion of blood pressure to these arteries and at the same time insures continuous blood flow to maintain patency of the graft.

While there has been shown and described the preferred embodiments of the graft of the invention, and method of supplying a continuous blood flow to one or more arteries, it is understood that changes in the materials, size, length of the graft, and location of the graft may be made by those skilled in the art without departing from the invention. The invention is defined in the following claims.

The embodiments of the invention in which an exclusive property or privilege is claimed are defined as follows:

1. A method for providing a continuous supply of flowing blood to at least one popliteal artery of a living body with an elongated biocompatible vascular graft having an inlet end and outlet end, a continuous passage extended from the inlet end to the outlet end for accommodating a continuous flow of blood and blood flow restriction means in the outlet portion thereof comprising: securing the inlet end of the graft to a femoral artery to supply blood under pressure to said passage to allow blood to flow in said continuous passage, securing at least one portion of the graft between the inlet end and the restriction means to at least one popliteal artery to continuously supply blood to said popliteal artery, and securing the outlet end of the graft to a popliteal vein whereby a continuous flow of blood flows through said passage from the inlet to the outlet end thereof and into said popliteal vein, said blood flow restriction means being operable to maintain flowing blood at a pressure in said passage sufficient to perfuse the popliteal artery.

2. The method of claim 1 wherein: a plurality of portions of said graft between the restriction means and the inlet end are anastomosed to separate popliteal arteries to continuously supply to said popliteal arteries.

3. A method of providing a continuous supply of flowing blood from an artery to at least one popliteal artery of a living body with an elongated bilocompatible vascular graft comprising a single tubular member having an inlet end, an outlet end, a single continuous passage extended from the inlet end to the outlet end for accommodating a continuous flow of blood, and a blood flow restriction section in a outlet portion thereof for maintaining flowing blood at a pressure sufficient to perfuse the blood receiving popliteal artery comprising: securing the inlet end of the tubular member to an artery in a manner to allow blood to flow from the artery into said continuous passage, securing at least one portion of the tubular member between the inlet end and restriction section to at least one popliteal artery, said portion having a hole to allow blood to flow from said continuous passage into said popliteal artery, and securing the outlet end of the tubular member to a popliteal vein having blood pressure less than the blood pressure of the supply of blood from the artery whereby continuous flow of blood flows through said continuous passage from the inlet end to the outlet end thereof into the second blood receiving vessel, said blood flow restriction section being operable to maintain flowing blood at a pressure in said passage sufficient to perfuse the popliteal artery.

4. A method of claim 3 including: securing separate portions of the tubular member between the inlet ends and restriction section to separate popliteal arteries to supply said popliteal arteries with blood.

5. The method of claim 3 wherein: said inlet end of the tubular member is secured to the femoral artery.

6. The method of claim 3 wherein: the inlet end of the tubular member is secured to the femoral artery and a plurality of portions of the tubular member between the inlet end and restriction section are anastomosed to separate popliteal arteries.

7. A method of providing a continuous supply of flowing blood from an artery to at least one peroneal artery of a living body with an elongated bilocompatible vascular graft comprising a single tubular member having an inlet end, and outlet end, a single continuous passage extend-d from the inlet end to the outlet end for accommodating a continuous flow of blood, and a blood flow restriction section in a outlet portion thereof for maintaining flowing blood at a pressure sufficient to perfuse the blood receiving peroneal artery comprising: securing the inlet end of the tubular member to an artery in a manner to allow blood to flow from the artery into said continuous passage, securing at least one portion of the tubular member between the inlet end and restriction section to at least one peroneal artery, said portion having a hole to allow blood to flow from said continuous passage into said peroneal artery, and securing the outlet end of the tubular member to a popliteal vein having blood pressure less than the blood pressure of the supply of blood from the artery whereby continuous flow of blood flows through said continuous passage from the inlet end to the outlet end thereof into the second blood receiving vessel, said blood flow restriction section being operable to maintain flowing blood at a pressure in said passage sufficient to perfuse the peroneal artery.

8. A method of claim 7 including: securing separate portions of the tubular member between the inlet ends and restriction section to separate peroneal arteries to supply said peroneal arteries with blood.

9. The method of claim 7 wherein: said inlet end of the tubular member is secured to the femoral artery.

10. The method of claim 7 wherein: the inlet end of the tubular member is secured to the femoral artery and a plurality of portions of the tubular member between the inlet end and restriction section are anastomosed to separate peroneal arteries.

* * * * *

UNITED STATES PATENT AND TRADEMARK OFFICE
CERTIFICATE OF CORRECTION

PATENT NO. : 4,562,597
DATED : January 7, 1986
INVENTOR(S) : Zinon C. Possis and Demetre M. Nicoloff It is certified that error appears in the above-identified patent and that said Letters Patent is hereby corrected as shown below:

Column 1, line 21, "continuous" should be --continues--.

Column 4, line 46, "vena ceva" should be --vena cava--.

Column 4, line 62, "17" should be --27--.

Column 6, line 31, "16" should be --46--.

Column 6, line 59, "1000" should be --100--.

Column 7, line 31, "sie" should be --size--.

Column 7, line 48, "anastoimosed" should be --anastomosed--.

Column 7, line 61, "Refering" should be --Referring--.

Column 8, line 2, "92" should be --93--.

Column 8, line 32, "The" should be --This--.

Signed and Sealed this

Twenty-second Day of July 1986

[SEAL]

Attest:

DONALD J. QUIGG

Attesting Officer

Commissioner of Patents and Trademarks